United States Patent [19]

Kreidl et al.

[11] Patent Number: 5,707,976
[45] Date of Patent: Jan. 13, 1998

[54] SUBSTITUTED PROPANE-2-OL DERIVATIVES

[75] Inventors: János Kreidl; Csaba Szántay; László Czibula; Mária née Kirják Farkas; Ida née Juhász Deutsch; Mihály Szegedi; István Hegedüs, all of Budapest, Hungary

[73] Assignee: Richter Gedeon Vegyeszeti Gyar Rt., Budapest, Hungary

[21] Appl. No.: 605,052

[22] PCT Filed: Sep. 22, 1994

[86] PCT No.: PCT/HU94/00040

§ 371 Date: Mar. 4, 1996

§ 102(e) Date: Mar. 4, 1996

[87] PCT Pub. No.: WO95/08552

PCT Pub. Date: Mar. 30, 1995

[30] Foreign Application Priority Data

Sep. 23, 1993 [HU] Hungary .................. P9302679

[51] Int. Cl.⁶ .................. A61K 31/695; C07F 7/18
[52] U.S. Cl. .................. 514/63; 548/110
[58] Field of Search .................. 548/110; 514/63

[56] References Cited

U.S. PATENT DOCUMENTS

| | | |
|---|---|---|
| 4,729,986 | 3/1988 | Olson .................. 514/63 |
| 5,495,024 | 2/1996 | Itoh et al. .................. 548/267.8 |

*Primary Examiner*—Patricia L. Morris
*Attorney, Agent, or Firm*—Herbert Dubno Jonathan Myers

[57] ABSTRACT

Anti-Fungal compounds are disclosed of the Formula (I)

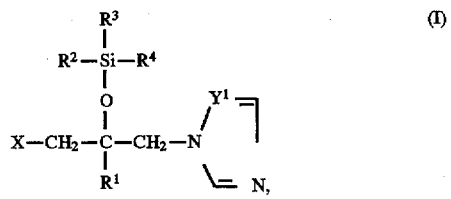

wherein $R^1$ is $C_1$ to $C_{10}$ alkyl, phenyl, or phenyl-$C_1$ to $C_6$ alkyl, and the phenyl moiety of the two latter groups may carry at least one substituent selected from the group consisting of a halogen atom, $C_1$ to $C_6$ alkoxy group, phenyl group, phenoxy group, and trifluoromethyl group;

$R^2$ is a hydrogen atom, a $C_1$ to $C_{10}$ alkyl group or a phenyl group;

$R^3$ and $R^4$ are independently from each other a $C_1$ to $C_{10}$ alkyl group or a phenyl group;

X is a hydrogen atom, halogen atom or a group of the formula (A)

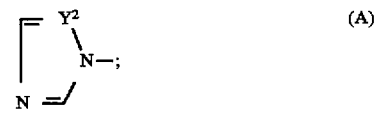

and in this formula $Y^1$ and $Y^2$ are independently from each other, a —N= atom or a group of the formula —CH=, or an optical antipode thereof.

9 Claims, No Drawings

SUBSTITUTED PROPANE-2-OL DERIVATIVES

The invention relates to novel substituted propane-2-ol derivatives, optical antipodes and racemates thereof, fungicidal compositions containing such compounds as well as to processes for preparing such compounds and compositions. Furthermore, the invention relates to a method of treating diseases caused by fungi, said method comprises administering one or more of the compounds of the present invention in a fungicidally effective amount to a mammal, by using a compound of the invention per se or in the form of a pharmaceutical composition.

The compounds of the present invention are characterized by the formula (I)

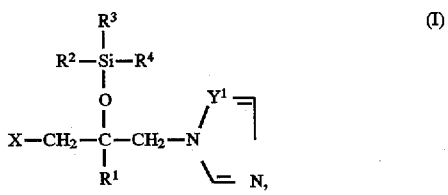

wherein $R^1$ is a $C_{1-10}$alkyl group, a phenyl group or a phenyl-$C_{1-6}$alkyl group, and the phenyl moiety of the two latter groups may carry at least one substituent selected from the group consisting of a halogen atom, $C_{1-6}$alkoxy group, phenyl group, phenoxy group and trifluoromethyl group;

$R^2$ is a hydrogen atom, a $C_{1-10}$alkyl group or a phenyl group;

$R^3$ and $R^4$ are independently from each other, a $C_{1-10}$alkyl or phenyl group;

X is a hydrogen atom, halogen atom or a group of the formula (A)

and in this formulae $Y^1$ and $Y^2$ are, independently from each other, a —N= atom or a group of the formula —CH=.

The compounds of the formula (I) carrying different substituents in positions 1 and 3 of the basic propane skeleton may exist in the form of optical antipodes. A 1:1 mixture of the antipodes forms a racemic mixture. If there is no reference to an individual antipode, it is self-evident that all the possible three forms are comprised by a reference to a compound of the formula (I). During the preparation process of the compounds of the formula (I) a racemic mixture thereof is formed. From this mixture the individual antipodes can be separated in a manner known per se, e.g. by selective crystallization of a diastereomeric salt pair formed with an optically active compound and then by liberation of the optically active compound of the formula (I).

GB patent specification No. 2,078,719 A relates to highly effective fungicidal compounds, possessing substantial plant growth regulating effect, too. These compounds are characterized by the formula

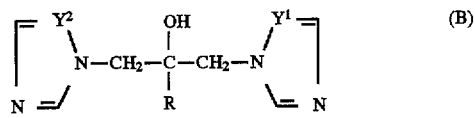

if R is an alkyl, cycloalkyl, aryl or aralkyl, all these groups being optionally substituted by one or two halogen(s), or said aryl or aralkyl groups may carry alkoxy, phenyl, phenoxy or trifluoromethyl substituents; and $Y^1$ and $Y^2$ are as defined above.

According to the GB patent specification No. 2,099,818 A, 2-(2,4-difluorophenyl)-1,3-bis(1,2,4-triazol-1-yl) propane-2-ol is used as a highly effective human fungicide. It is sold in the form of a human fungicidal pharmaceutical composition under the trade name fluconazole or diflucane.

In accordance with the GB patent specification No. 2,078, 719 A the propane-2-ol derivatives of the formula (B) can be prepared by reacting a Grignard reagent of the formula R-Mg-halogen with dichloroacetone. A thus-obtained 1,3-dichloropropane-2-ol derivative of the formula

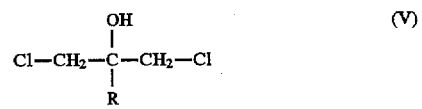

is reacted with a salt, e.g. sodium salt, of imidazole or triazole, taken in an excess, in the presence of a protic or aprotic solvent, e.g. dimethyl formamide. The reaction can be also carried out with epoxy derivatives being prepared in situ through elimination of hydrogen chloride from the corresponding dihalogen compound with a base. The target compounds can be prepared by reacting the corresponding 1,3-bisimidazolyl- or 1,3-bis(1,2,4-triazol-1-yl)acetone with a Grignard reagent of the formula R-Mg-halogen, too. According to a further preparation method a compound of the formula

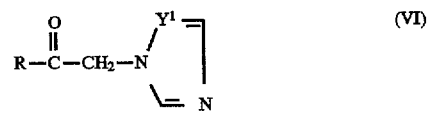

is reacted with dimethyloxosulfoniummethylide, then a thus-obtained compound of the formula

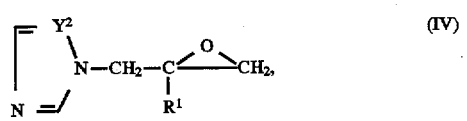

containing an R substituent in the place of $R^1$, is reacted, similarly to the process described above, with the sodium salt of imidazole or triazole. The starting materials of the above processes can be prepared by known methods.

The process for the preparation of the active ingredient of fluconazole according to GB patent specification No. 2,099, 818 A comprises the reaction of compounds of the formula (V) and compounds of the formula (IV) containing a substituent R in the place of $R^1$, too but instead of 1,2,4-triazol-1-yl sodium, a base and triazole are used as reactants.

A common feature of the processes described in the GB patent specifications Nos. 2,078,719 A and 2,099,818 A resides in that when isolating the target compounds the reaction mixture is first diluted with water, then extracted and the product is isolated and purified by known methods like column chromatography or fractioning in vacuo, etc. The yields amount to about 30–50%.

In accordance with the GB patent specification No. 2,078, 719 A the esters and ethers of the target alcohols can be prepared by reacting the salt of the alcohol, formed with sodium hydride, with a corresponding acylating or alkylating agent.

During tests carried out with the active ingredient of fluconazole, used in a high volume in view of its very substantial human fungicidal action of wide spectrum, it was established that said active ingredient has a relatively weak effect against the very wide-spread pathogenic fungus *Candida albicans*. Mainly this resistant species causes the disease called "candidiasis" which is quite wide-spread and very difficult to influence. According to our in vitro tests the active ingredient of floconazole ensures a full inhibition against other Candida species and other pathogenic fungi in a very low dose, i.e. 0.1 to 10 µg/ml; however, in the case of *Candida albicans* this inhibiting effect occurs only at a dose of 2500 µg/ml.

During our research work with the purpose of obtaining fungicidal agents of increased effect with a broader spectrum it was surprisingly recognized that the silyl ether derivatives of the formula (I) possess a surprisingly high fungicidal action of a broad spectrum. This broad spectrum appears mainly in the case of fungus strains infecting humans. For example, the trimethyl silyl ether corresponding to the active ingredient of fluconazole is times more effective against *Candida albicans* than said active ingredient of fluconazole. This increased activity can be established in the case of a very broad spectrum of pathogenic fungi.

Thus, the first object of the present invention relates to propane-2-ol derivatives of the formula (I)

$$\begin{array}{c} R^3 \\ | \\ R^2-Si-R^4 \\ | \\ O \\ | \\ X-CH_2-C-CH_2-N \diagup \!\!\!\diagdown \\ | \qquad\qquad\qquad\quad \diagdown\!\!\!= N, \\ R^1 \end{array} \qquad (I)$$

wherein $R^1$ is a $C_{1-10}$alkyl group, a phenyl group or a phenyl-$C_{1-6}$alkyl group, and the phenyl moiety of the two latter groups may carry at least one substituent selected from the group consisting of a halogen atom, $C_{1-6}$alkoxy group, phenyl group, phenoxy group and trifluoromethyl group;

$R^2$ is a hydrogen atom, a $C_{1-10}$alkyl group or a phenyl group;

$R^3$ and $R^4$ are, independently from each other, a $C_{1-10}$alkyl or phenyl group;

X is a hydrogen atom, halogen atom or a group of the formula (A)

$$\begin{array}{c} \diagup\!\!\!= Y^2 \\ \qquad\quad \diagdown \\ \qquad\qquad N-; \\ N =\diagup \end{array} \qquad (A)$$

and in this formulae $Y^1$ and $Y^2$ are, independently from each other, a —N= atom or a group of the formula —CH=, and optical antipodes and racemates thereof.

Further, it was recognized that the propane-2-ol derivatives of the formula (I) can be prepared through the addition of a silyl triazole or silyl imidazole derivative of the formula $$\begin{array}{c} R^4 \quad Y^1 =\!\!\!\diagdown \\ | \quad \diagup \\ R^3-Si-N \\ | \qquad\qquad \diagdown\!\!\!= N, \\ R^2 \end{array} \qquad (III)$$

wherein $Y^1$, $R^2$, $R^3$ and $R^4$ are as defined above, to an (II), epoxide derivative of the formula $$\begin{array}{c} O \\ \diagup \diagdown \\ X-CH_2-C-\!\!\!-CH_2, \\ | \\ R^1 \end{array} \qquad (II)$$

wherein X and $R^1$ are as defined above, or $$\begin{array}{c} \diagup\!\!\!= Y^2 \\ \qquad\quad \diagdown \qquad\qquad O \\ \qquad\qquad N-CH_2-C\!\!\diagup\!\!\!\diagdown\!\!CH_2, \\ N =\diagup \qquad\qquad\qquad | \\ \qquad\qquad\qquad\qquad\quad R^1 \end{array} \qquad (IV)$$

wherein $Y^2$ and $R^1$ are as defined above, in the presence of a strongly basic catalyst.

Thus, the second object of the present invention is a process for the preparation of the propane-2-ol derivatives of the formula (I) and optical antipodes and racemates thereof. This process is characterized by a) reacting an epoxy derivative of the formula (II), wherein X and $R^1$ are as defined above, with a silyl derivative of the formula (III), wherein $R^2$, $R^3$, $R^4$ and $Y^1$ are as defined above, in the presence of a strong base; or b) reacting an epoxy derivative of the formula (IV), wherein $Y^2$ and $R^1$ are as defined above, with a silyl derivative of the formula (III), wherein $R^2$, $R^3$, $R^4$ and $Y^1$ are as defined above, in the presence of a strong base to obtain compounds of the formula (I) containing a group of the formula (A) as X;

and, if desired, resolving a compound of the formula (I) obtained in the form of a racemate.

The additions according to processes a) and b) proceed, irrespectively from the meanings of $R^1$, $R^2$, $R^3$, $R^4$, X, $Y^1$ and $Y^2$, quickly and with a very good (65 to 85%) efficiency.

The reactions are performed in an aprotic medium, preferably aprotic dipolar medium, e.g. dimethyl formamide. As a catalyst strong bases like potassium carbonate or potassium tert-butylate, or an alkali metal salt of triazole or imidazole, can be used.

According to process a) it is possible that only the epoxide group of a compound of the formula (II) is brought into reaction with a silyl derivative of the formula (III), while the halogen atom in the place of X remains unchanged. In this case only 0.01 to 0.1 mole % of a strong base is used in addition to the excess of the silyl derivative of the formula (III), and the reaction is performed at lower (50° to 70° C.) temperatures. In such a manner a target compound of the formula (I) containing a chloro atom as X can be very efficiently prepared.

Should the halogen atom in the place of, X in the starting materials of the formula (II) be replaced by a triazolyl or imidazolyl group, a compound of the formula $$\begin{array}{c} Y =\!\!\!\diagdown \\ \diagup \\ Z-N \\ \qquad\quad \diagdown\!\!\!= N, \end{array} \qquad (VII)$$

wherein Z is an alkali metal, preferably sodium or potassium, and the meaning of Y is identical to that of $Y^1$ and $Y^2$ as defined before, containing a heteroaromatic group corresponding to that to be introduced to the place of X, is used as a strong base in a molar amount of 1.01 to 1.10.

According to process b) it is also possible that only the epoxide group of a compound of the formula (IV) is brought into reaction by using a corresponding silyl derivative of the formula (III) in an amount corresponding at least to the equimolar amount, suitably in an excess of 10 to 100%, in the presence of 0.01 to 0.10 mole % of a strong base.

By appropriately selecting the starting materials of the formulae (II), (III), (IV) and (VII) and the reactants one can prepare substituted propane-2-ol derivatives of the formula (I) containing two identical or different heteroaromatic groups.

The compounds of the formulae (II) and (IV) used as starting materials are either known from the GB patent specification No. 2,099,818 A or can be prepared by well-known methods. For example, epoxy derivatives of the formula (II) containing a hydrogen atom as X can be prepared by reacting a Grignard reagent of the formula $R^1$-Mg-halogen with chloroacetone in analogous manner to the process carried out with dichloroacetone and treating the obtained product with a base.

When subjecting the silyl ether bond of the substituted propane-2-ol derivatives of the formula (I) to stability examinations it was stated they are practically stable in the presence of water (in aqueous solution) in a pH range of 3 to 8, i.e. a range corresponding to that of the human organism. After a storage of 50 hours at room temperature less than 10% of the amount of a compound of the invention decomposes through hydrolysis.

In contrast, the esters and ethers disclosed in the GB patent specification 2,078,719 A suffer hydrolysis in the presence of water by a speed higher with orders of magnitude.

The fungicidal action of the compounds of the formula (I) was examined in the following in vitro tests.

Densitometric measurement of the propagation of yeast fungi

A microbiological analyzer called BIOSCREEN C (LAB-SYSTEMS, Helsinki, Finland) was used to the measurements. From the test compounds first a stock solution of a concentration of 50 mg/ml, then in 15 steps a bisecting dilution series was prepared with dimethyl sulfoxide. From every dilution step 10 µl each was introduced into the cells of the analysator. Then 390 µl of an aqueous nutrient solution was piperred into the cells. In the mixtures obtained the cells of the yeasts, e.g. Candida albicans, cans, were suspended in such an amount that the optical density of the suspension obtained be about 0.1. Young cultures, shaken at 30° C. for about 12 hours, were used in the preparation of the suspensions. The composition of the aqueous nutrient solution was as follows: 1% by weight of glucose, 0.5% by weight of yeast extract (a product of the firm OXOID Ltd, Great Britain, under the catalogue No. L21) and 0.5% by weight of nutrient broth (a product of the firm OXOID Ltd, Great Britain, under the catalogue No. CM ½). The concentration of the compounds to be tested in the cells corresponded to 1250, 625, 312, 156, 78, 39, 19, 9, 4, 2, 1, 0.6, 0.3, 0.15 and 0.07 µg/ml, resp. The densitometric measurement of the cultures was carried out during an incubation at 37° C. for 30 hours. The change in the turbidity of the culture, which can be followed through optical measurement, is proportional to the propagation of the yeast fungi.

As the minimal inhibitory concentration (MIC) of this test that minimal concentration of the tested compound was determined which was able to prevent totally the propagation of the fungus. The obtained results are given in the following Table.

TABLE

| MIC values [µg/ml] of the individual tests | |
|---|---|
| Active agent | Candida albicans |
| compound of Example 1 | 150 |
| compound of Example 3 | 150 |
| compound of Example 5 | 9 |
| compound of Example 6 | 150 |
| compound of Example 8 | 19 |
| flucohazole | 2500 |

Thus, the third object of the present invention is a method of treating fungicidal infections of mammals. This method is characterized by administering a fungicidally effective amount of one or more of the novel propane-2-ol derivatives of the formula (I) or an optical antipode or racemate thereof to said mammal, optionally together with a pharmaceutically acceptable carrier and/or other adjuvant.

The therapeutic use of the compounds of the formula (I) is suitable in the case of all the diseases where the main aim is the control of a pathogenic fungus being already present in the organism. The compounds of the present invention can be used both in the human and veterinary therapies. During such therapies the daily oral or parenteral dose of the compounds of the formula (I) is about 0.1 to 10 mg/kg, by administering said dose at once or in divided subdoses.

The fourth object of the present invention relates to pharmaceutical compositions of fungicidal action. These compositions are characterized by containing a fungicidally effective amount of one or more of the compounds of the formula (I) or an optical antipode or racemate, together with a pharmaceutically acceptable carrier and/or other adjuvant.

These pharmaceutical compositions are prepared by known methods and are suitable for parenteral or enteral use. The carriers may be non-toxic inert solid or liquid carriers like water, gelatin, milk sugar, starch, pectine, magnesium stearate, talc and vegetal oils.

These pharmaceutical compositions can be prepared in the usual forms, mainly in solid forms, like rounded-off or angular tablets, dragées, capsules (e.g. gelatin capsules), pilules and suppositories.

Based on one tablet the amount of the solid active agent may vary in a wide range, preferably between 25 mg and 1 g. In addition to the carriers these pharmaceutical compositions may contain usual pharmaceutical additives like preservatives.

The pharmaceutical compositions of the invention can be prepared by known methods, as in the case of solid compositions through sieving, mixing, granulating and optionally pressing the components. The thus-obtained compositions may be subjected to the usual pharmaceutical post-treatments such as sterilization in the case of injections.

The present invention is elucidated by the aid of the following non-limiting examples.

EXAMPLE 1

2-(2,4-Difluorophenyl)-1,3-bis(1,2,4-triazol-1-yl)-2-(trimethylsilyloxy)propane

Under nitrogen atmosphere 11.85 g (0.05 moles) of 1,2-epoxy-2-(2,4-difluorophenyl)-3-(1,2,4-triazol-1-yl) propane (prepared in accordance with the process described in GB patent specification No. 2,099,818 A) are reacted with 9.16 g (0.065 moles) of 1-(trimethylsilyl)-1,2,4-triazole and 0.01 g (0.12 mmoles) of 1,2,4-triazol-1-yl sodium in 100 ml of dimethyl formamide for 1 hour at 80° C. The reaction mixture is cooled to room temperature, neutralized with glacial acetic acid and mixed with 500 ml of water. The aqueous mixture is extracted twice with 100 ml of dichloromethane each. The combined extracts are washed three times with 100 ml of water each, dried over water-free sodium sulfate and evaporated to solvent-free in vacuo. The evaporation residue is crystallized from 60 ml of n-hexane containing 5% by volume of ethyl acetate. 16.065 g (85%) of the title compound are obtained; m.p.: 69°–71° C.

EXAMPLE 2

2-(2,4-Difluorophenyl)-1,3-bis(1,2,4-triazol-1-yl)-2-(trimethylsilyloxy)-propane Under nitrogen atmosphere 10.3 g (0.05 moles) of 1,2-epoxy-3-chloro-2-(2,4-difluorophenyl) propane are reacted with 14.1 g (0.1 mole) of 1-(trimethylsilyl)-1,2,4-triazole and 4.78 g (0.0525 moles) of 1,2,4-triazol-1-yl sodium in 100 ml of dimethyl formamide for 1.5 hours at 100° C. The reaction mixture is then diluted with 600 ml of water and the aqueous mixture is extracted three times with 100 ml of dichloromethane each. The combined extracts are washed three times with 100 ml of water each, dried over water-free sodium sulfate and evaporated to solvent-free in vacuo. The evaporation residue is crystallized from 50 ml of ethyl acetate. 13.42 g (71%) of the title compound are obtained; m.p.: 69°–71° C.

EXAMPLE 3

1-(Imidazol-1-yl)-2-(2,4-difluorophenyl)-3-(1,2,4-triazol-1-yl)-2-(trimethylsilyloxy) propane 4.74 g (.0.02 moles) of 1,2-epoxy-2-(2,4-difluorophenyl)-3-(1,2,4-triazol-1-yl) propane are heated at 80° C. for 1 hour in 40 ml of acetonitrile with 3.36 g (0.024 moles) of N-(trimethylsilyl)imidazole and 0.055 g (0.5 mmoles) of potassium tert-butylate. The reaction mixture is then cooled back to room temperature, neutralized with glacial acetic acid and evaporated to solvent-free in vacuo. The evaporation residue is crystallized from 25 ml of 1:1 by volume mixture of ethyl acetate and n-hexane. 6.18 g (82%) of the title compound are obtained; m.p.: 87°–89°C.

EXAMPLE 4

2-(2,4-Difluorophenyl)-1,3-bis(imidazol-1-yl)-2-(trimethylsilyloxy) propane 10.3 g (0.05 moles) of 1,2-epoxy-2-(2,4-difluorophenyl)-3-chloropropane are reacted in 100 ml of dimethyl formamide at 100° C. for 1 hour with 4.68 g (0.052 moles) of imidazol-1-yl sodium and 21.0 g (0.15 moles) of N-(trimethylsilyl)imidazole. The reaction mixture is evaporated to half of its original volume in vacuo. The evaporation residue is neutralized with glacial acetic acid and mixed with 250 ml of water. The obtained aqueous mixture is extracted three times with 20 ml of dichloromethane each. The combined extracts are washed twice with 50 ml of water each, dried over water-free sodium sulfate and evaporated in vacuo. The evaporation residue is subjected to column chromatography on a column filled with "Kieselgel 40" (particle size: 70–230 mesh) of the firm Merck by using a 20:1 by volume mixture of ethyl acetate and methanol as eluting agent. The fractions proved to be pure by thin layer chromatography are combined and evaporated to solvent-free. The evaporation residue is crystallized from 60 ml of n-hexane. 13.96 g (73.2%) of the title compound are obtained; m.p.: 134°–136° C.

EXAMPLE 5

1-Chloro-2-(2,4-difluorophenyl)-3-(1,2,4-triazol-1-yl)-2-(trimethylsilyloxy) propane 4.11 g (0.02 moles) of 1,2-epoxy-2-(2,4-difluorophenyl)-3-chloropropane are reacted with 4.23 g (0.03 moles) of 1-(trimethylsilyl)-1,2,4-triazole and 0.1 g (0.001 mole) of 1,2,4-triazol-1-yl potassium in 50 ml of dimethyl formamide at 50° C. for 2 hours. Then the reaction mixture is neutralized by glacial acetic acid, mixed with 250 ml of water at room temperature and extracted twice with 50 ml of dichloromethane each. The combined extracts are washed three times with 50 ml of water each, dried over water-free sodium sulfate and evaporated in vacuo. The residue is subjected to column chromatography by the method of Example 4 above. After crystallization from n-heptane 4.9 g (71.5%) of the title compound are obtained; m.p.: 59°–61° C.

EXAMPLE 6

2-(2,4-Difluorophenyl)-3-(1,2,4-triazol-1-yl)-2-(trimethylsilyloxy)propane 5.13 g (0.03 moles) of 1,2-epoxy-2-(2,4-difluorophenyl)-propane are reacted with 6.35 g (0.045 moles) of 1-(trimethylsilyl)-1,2,4-triazole and 0.14 g (0.0015 moles) of 1,2,4-triazol-1-yl sodium in 40 ml of dimethyl formamide at 80° C. for 3 hours. Then the reaction mixture is cooled to room temperature, neutralized by glacial acetic acid, mixed with 200 ml of water and extracted twice with 50 ml of dichloromethane each. The combined extracts are washed three times with 50 ml of water each, dried over water-free sodium sulfate and evaporated in vacuo. After carrying out a separation as described in Example 5, removal of the solvent and crystallization from n-heptane 6.0 g (64.5%) of the title compound are obtained; m.p.: 51°–53° C.

EXAMPLE 7

2-(2,4-Dichlorophenyl)-1-(1,2,4- triazol -1-yl)-3-(imidazol-1-yl)-2-(trimethylsilyloxy) propane 11.85 g (0.05 moles) of 1,2-epoxy-2-(2,4-dichlorophenyl)-3-(1,2,4-triazol-1-yl) propane are reacted with 9.8 g (0.07 moles) of N-(trimethylsilyl)imidazole and 0.02 g (0.24 mmoles) of imidazol-1-yl sodium in 100 ml of dimethyl formamide at 80° C. for 1 hour. Then the reaction mixture is treated as disclosed in Example 1. 14.86 g (73.2%) of the title compound are obtained; m.p.: 82°–85° C.

EXAMPLE 8

1-Chloro-2-(2,4-difluorophenyl)-3-(imidazol-1-yl)-2-(trimethylsilyloxy)propane 4.11 g (0.02 moles) of 1,2-epoxy-3-chloro-2-(2,4-difluorophenyl)propane are reacted with 4.20 g (0.03 moles) of N-(trimethylsilyl)imidazole and 0.09 g (0.001 mole) of imidazol-1-yl sodium in 40 ml of dimethyl formamide at 60° C. for 2 hours. Then the reaction mixture is neutralized with glacial acetic acid and evaporated in vacuo. The evaporation residue is mixed with 50 ml of water. The aqueous mixture is extracted with 40 ml of dichloromethane. The title compound is recovered from the extract by the column chromatography disclosed in Example 4. 4.96 g (72%) of the title compound are obtained; m.p.: 88°–89° C.

EXAMPLE 9

2-(2,4-Difluorophenyl)-3-(imidazol-1-yl)-2-(trimethylsilyloxy)propane 5.00 g (29.2 mmoles) of 1,2-epoxy-2-(2,4-difluorophenyl)-propane are reacted with 6.4 g of N-(trimethylsilyl) imidazole and 0.13 g (1.46 mmoles) of imidazol-1-yl sodium in 40 ml of dimethyl formamide at 70° C. for 1.5 hours. Then the reaction mixture is cooled back to room temperature, neutralized with glacial acetic acid and evaporated in vacuo. The evaporation residue is mixed with 50 ml of water and the aqueous mixture is extracted with 50 ml of dichloromethane. The title compound is recovered from the extract by column chromatography disclosed in Example 4. 5.6 g (62%) of the title compound of oily nature are obtained; $n^{20}D$: 1.4935.

EXAMPLE 10

Tablets of a weight of 100 mg, containing 10 mg of active ingredient 50.0 g of active ingredient, 285.0 g of lactose, 100.0 g of potato starch, 2.5 g of sodium dodecyl sulphate, 5.0 g of polyvinylpyrrolidone (Kollidon-K 90®), 50.0 g of microcrystalline cellulose (Avicel®) and 7.5 g of vegetable oil (Sterotex®)

are compressed in a known manner to tablets of a weight of 100 mg by wet granulating and pressing. Each of these tablets contains 10 mg of active ingredient.

EXAMPLE 11

Dragées of a weight of 125 mg, containing 10 mg of active ingredient

The tablets prepared in accordance with the method of Example 10 are covered in a known manner with a covering comprising sugar and talc. Finally, they are polished with a mixture of beewax and carnaubawax.

EXAMPLE 12

Capsules containing 20 mg of active ingredient 40.0 g of active ingredient, 12.0 g of sodium lauryl sulphate, 102.0 g of lactose, 102.0 g of potato starch, 2.4 g of magnesium stearate, and 1.6 g of colloid silicon dioxide are thoroughly mixed together and the obtained mixture is filled into hard gelatine capsules, containing 20 mg of active ingredient each.

What we claim is:

1. A compound of the formula (I)

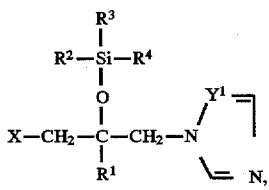

(I)

wherein $R^1$ is $C_{1-10}$alkyl group, a phenyl group or a phenyl-$C_{1-6}$alkyl group, and the phenyl moiety of the two latter groups may carry at least one substituent selected from the group consisting of a halogen atom, $C_{1-6}$ alkoxy group, phenyl group, phenoxy group and trifluoromethyl group;

$R^2$ is a $C_{1-10}$alkyl group or a;

$R^3$ and $R^4$ are, independently from each other, a $C_{1-10}$alkyl group;

X is a halogen atom or a group of the formula (A)

(A)

and in this formulae $Y^1$ and $Y^2$ are, independently from each other, a —N= atom or a group of the formula —CH=, or an optical antipode thereof.

2. 2-(2,4-Difluorophenyl)-1,3-bis(1,2,4-triazol-1-yl)-2-(trimethylsilyloxy)propane defined in claim 1.

3. 1-(Imidazol-1-yl)-2-(2,4-difluorophenyl)-3-(1,2,4-triazol-1-yl)-2-(trimethylsilyloxy) propane defined in claim 1.

4. 2-(2,4-Difluorophenyl)-1,3-bis(imidazol-1-yl)-2-(trimethylsilyloxy) propane defined in claim 1.

5. 1-Chloro-2-(2,4-difluorophenyl)-3-(1,2,4-triazol-1-yl)-2-(trimethylsilyloxy) propane defined in claim 1.

6. 1-Chloro-2-(2,4-difluorophenyl)-3-(imidazol-1-yl)-2-(trimethylsilyloxy) propane defined in claim 1.

7. 2-(2,4-Dichlorophenyl)-1-(1,2,4-triazol-1-yl)-3-(imidazol-1-yl)-2-(trimethylsilyloxy) propane defined in claim 1.

8. A pharmaceutical composition of fungicidal action which comprises a fungicidally effective amount of a compound of the formula (I), as defined in claim 1, or an optical antipode thereof, together with a pharmaceutically acceptable inert carrier.

9. A method of treating a fungicidal infection in a mammal which comprises the steps of administering to said mammal, a fungicidally effective amount of a compound of the formula (I) as defined in claim 1, or an optical antipode thereof, alone or in the form of a pharmaceutical composition.

* * * * *